United States Patent
Stock et al.

(10) Patent No.: US 10,363,767 B2
(45) Date of Patent: Jul. 30, 2019

(54) METHOD FOR MARKING A FEATURE SUBSTANCE, SECURITY FEATURE, DOCUMENT OF VALUE AND METHOD FOR VERIFYING SAID DOCUMENT

(71) Applicant: GIESECKE & DEVRIENT GMBH, Munich (DE)

(72) Inventors: Kai Uwe Stock, Grunwald (DE); Martin Stark, Munich (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 372 days.

(21) Appl. No.: 14/888,864

(22) PCT Filed: May 5, 2014

(86) PCT No.: PCT/EP2014/001197
§ 371 (c)(1),
(2) Date: Nov. 3, 2015

(87) PCT Pub. No.: WO2014/180557
PCT Pub. Date: Nov. 13, 2014

(65) Prior Publication Data
US 2016/0075163 A1    Mar. 17, 2016

(30) Foreign Application Priority Data
May 7, 2013   (DE) ........................ 10 2013 007 811

(51) Int. Cl.
*B42D 25/29*   (2014.01)
*G07D 7/1205*  (2016.01)
(Continued)

(52) U.S. Cl.
CPC ............. *B42D 25/29* (2014.10); *B41M 3/144* (2013.01); *B42D 25/00* (2014.10); *B42D 25/405* (2014.10);
(Continued)

(58) Field of Classification Search
CPC ...... B42D 25/29; B42D 25/405; B42D 25/00; B42D 2035/34; B42D 2033/20;
(Continued)

(56) References Cited

U.S. PATENT DOCUMENTS 4,452,843 A   6/1984  Kaule et al.
6,344,261 B1  2/2002  Kaule et al.
(Continued)

FOREIGN PATENT DOCUMENTS

DE    19804021 A1    8/1999
DE    10111116 A1    9/2002
(Continued)

OTHER PUBLICATIONS

German Search Report for corresponding German Application No. 102013007811.3, dated Jul. 3, 2013.
(Continued)

*Primary Examiner* — Justin V Lewis
(74) *Attorney, Agent, or Firm* — Workman Nydegger

(57) ABSTRACT

The invention concerns a method for marking a feature substance, present in particular in pulverized form, with at least one marker, with the feature substance being suitable for the authentication of value documents, comprising the step of mixing the feature substance with a small quantity of the marker present in the form of particles, so that the macroscopic detectability of the feature substance is not influenced by the marker and the marker is detectable in a value document having a security feature containing the marked feature substance by means of a spatially resolving
(Continued)

analytical method which is adapted to resolve down to the single-particle level.

18 Claims, 3 Drawing Sheets

(51) Int. Cl.
| | | |
|---|---|---|
| *G07D 7/00* | (2016.01) | |
| *G01N 23/223* | (2006.01) | |
| *G01N 21/65* | (2006.01) | |
| *B41M 3/14* | (2006.01) | |
| *B42D 25/405* | (2014.01) | |
| *B42D 25/00* | (2014.01) | |
| *C09K 11/68* | (2006.01) | |
| *C09K 11/77* | (2006.01) | |
| *D21H 21/30* | (2006.01) | |
| *D21H 21/40* | (2006.01) | |
| *G01N 23/20091* | (2018.01) | |

(52) U.S. Cl.
CPC ........ *C09K 11/681* (2013.01); *C09K 11/7708* (2013.01); *D21H 21/30* (2013.01); *D21H 21/40* (2013.01); *G01N 21/65* (2013.01); *G01N 23/20091* (2013.01); *G01N 23/223* (2013.01); *G07D 7/003* (2017.05); *G07D 7/1205* (2017.05); *B42D 2033/14* (2013.01); *B42D 2033/20* (2013.01); *B42D 2035/34* (2013.01)

(58) Field of Classification Search
CPC .. B42D 2033/14; G07D 7/1205; G07D 7/003; G01N 23/223; G01N 21/65; G01N 23/20091; C09K 11/7708; C09K 11/681; D21H 21/30; D21H 21/40; B41M 3/144
USPC ........ 283/67, 70, 72, 74, 75, 77, 78, 84, 88, 283/89, 91, 92, 94, 98, 901
See application file for complete search history.

(56) References Cited

U.S. PATENT DOCUMENTS

| | | |
|---|---|---|
| 6,643,001 B1 | 11/2003 | Faris |
| 6,802,992 B1 | 10/2004 | Wieczoreck et al. |
| 7,845,570 B2 | 12/2010 | Schwenk et al. |
| 8,333,870 B2 | 12/2012 | Burchard et al. |
| 8,663,820 B2 | 3/2014 | Giering et al. |
| 2004/0105962 A1 | 6/2004 | Giering et al. |
| 2005/0031838 A1 | 2/2005 | Lagunowich et al. |
| 2006/0127649 A1 | 6/2006 | Keller et al. |
| 2007/0158433 A1 | 7/2007 | Schwenk et al. |

FOREIGN PATENT DOCUMENTS

| | | |
|---|---|---|
| DE | 10346634 A1 | 5/2005 |
| DE | 102008034021 A1 | 1/2010 |
| DE | 102008034022 A1 | 1/2010 |
| EP | 000927749 A1 * | 7/1999 |
| EP | 0927749 A1 | 7/1999 |
| EP | 0966504 B1 | 11/2005 |
| FR | 2866460 A1 | 8/2005 |
| WO | 8103507 A1 | 12/1981 |
| WO | 9938701 A1 | 8/1999 |
| WO | 2004028825 A2 | 4/2004 |
| WO | 2006066431 A1 | 6/2006 |
| WO | 2011084663 A2 | 7/2011 |

OTHER PUBLICATIONS

International Preliminary Report on Patentability for corresponding International PCT Application No. PCT/EP2014/001197, dated Nov. 10, 2015.
International Search Report for corresponding International PCT Application No. PCT/EP2014/001197, dated Jul. 24, 2014.

* cited by examiner

METHOD FOR MARKING A FEATURE SUBSTANCE, SECURITY FEATURE, DOCUMENT OF VALUE AND METHOD FOR VERIFYING SAID DOCUMENT

BACKGROUND

The invention concerns a method for marking a feature substance, present in particular in pulverized form, with at least one marker. The invention furthermore concerns a security feature having the marked feature substance for the safeguarding of value documents, a value document having such a security feature, and a method for checking the authenticity and/or the origin of the value document.

The safeguarding of value documents against forgery by means of security features has been known for some time. Feature substances are known that are based e.g. on magnetic, thermal, electrical and/or optical (e.g. absorption and emission) effects, through which the specific detectability is guaranteed.

Of special importance are luminescent feature substances. In such substances the luminescent components used are substances (which will hereinafter also be designated as luminophores) that are able to emit light with a characteristic spectral distribution after excitation (e.g. by light, heat or by an electrical field). They are preferably formed from host lattices doped with transition metals or rare earth metals as luminescent ions (there also being employed hereinafter the term matrix instead of the term host lattice). For the doping, combinations of transition metals and/or rare earth metals have also been discussed, see e.g. WO 99/38701. Transition metals ions or rare earth metal ions have the advantage that, after being suitably excited, they show one or more characteristic luminescences which facilitate a reliable proof and the delimitation over other spectra. The emission of the employed luminophores is also designated as luminescence, whereby this may involve fluorescence and/or phosphorescence.

The security features are incorporated into and/or applied to value documents in different forms of use. In particular, in the case of luminescent feature substances there can also be employed a combination of luminophores whose emissions differ with respect to their spectral and/or temporal properties. The emission bands of the employed luminophores constitute a spectral coding.

SUMMARY

The invention is based on the object of developing the component(s) of the feature substance so as to enable batch tracking, an identification of the place of production or manufacturer. In particular, there is to be enabled the assignment to a manufacturer in order to thereby guarantee an improved retraceability of the safeguarding elements contributing to the value document. Furthermore, there is to be enabled in particular the recognition of simulated components.

1. (First aspect) A method for marking a feature substance, present in particular in pulverized form, with at least one marker, with the feature substance being suitable for the authentication of value documents, comprising the step of mixing the feature substance with a small quantity of the marker present in the form of particles, so that the macroscopic detectability and identifiability of the feature substance is not influenced by the marker and the marker is detectable in a value document having a security feature containing the marked feature substance by means of a spatially resolving analytical method which is adapted to resolve down to the single-particle level.

The formulation "the macroscopic detectability and identifiability of the feature substance is not influenced by the marker" is intended to mean in particular that the measurement-signal magnitude or measurement-signal intensity forming the basis for the respective method for checking the authenticity of the value document or for the macroscopic detection or identification of the feature substance (e.g. the measured luminescence intensity of a luminescent feature substance) changes less than 5%, preferably less than 2%, and particularly preferably less than 1%, through the presence of the marker.

2. (Preferred) The method according to item 1, wherein the content of the marker lies in a range of 0.1 to 10 wt. %, preferably 1 to 5 wt. %, based on the total weight of the marked feature substance.
3. (Preferred) The method according to item 1 or 2, wherein the feature substance is a luminescent feature substance.
4. (Preferred) The method according to item 3, wherein the marker is a luminescent marker.
5. (Preferred) The method according to item 4, wherein the emission of the luminescent marker occurs in another spectral wavelength region compared to the emission of the marked luminescent feature substance.
6. (Preferred) The method according to item 4 or 5, wherein the luminescent marker is excitable in another spectral wavelength region than the marked luminescent feature substance.
7. (Preferred) The method according to any of items 4 to 6, wherein the luminescent marker and the marked luminescent feature substance respectively have a different lifetime of luminescence.
8. (Preferred) The method according to any of items 1 to 7, wherein the grain size (D99) of the marker lies in a range of 1 to 30 μm.
9. (Preferred) The method according to any of items 1 to 8, wherein the spatially resolving analytical method is confocal laser microscopy or multiphoton microscopy.
10. (Preferred) The method according to any of items 1 to 8, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.
11. (Second aspect) A security feature for the safeguarding of value documents, comprising a marked feature substance which is obtainable by mixing the feature substance present in particular in pulverized form, and suitable for the authentication of value documents, with a small quantity of a marker present in the form of particles, so that the macroscopic detectability and identifiability of the feature substance is not influenced by the marker and the marker is detectable in a value document having the security feature by means of a spatially resolving analytical method which is adapted to resolve down to the single-particle level.
12. (Preferred) The security feature according to item 11, wherein the content of the marker lies in a range of 0.1 to 10 wt. %, preferably 1 to 5 wt. %, based on the total weight of the marked feature substance.
13. (Preferred) The security feature according to item 11 or 12, wherein the feature substance is a luminescent feature substance.
14. (Preferred) The security feature according to item 13, wherein the marker is a luminescent marker.

15. (Preferred) The security feature according to item 14, wherein the emission of the luminescent marker occurs in another spectral wavelength region compared to the emission of the marked luminescent feature substance.
16. (Preferred) The security feature according to item 14 or 15, wherein the luminescent marker is excitable in another spectral wavelength region than the marked luminescent feature substance.
17. (Preferred) The security feature according to any of items 14 to 16, wherein the luminescent marker and the marked luminescent feature substance respectively have a different lifetime of luminescence.
18. (Preferred) The security feature according to any of items 11 to 17, wherein the grain size (D99) of the marker lies in a range of 1 to 30 μm.
19. (Preferred) The security feature according to any of items 11 to 18, wherein the spatially resolving analytical method is confocal laser microscopy or multiphoton microscopy.
20. (Preferred) The security feature according to any of items 11 to 18, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.
21. (Third aspect) A value document, in particular a bank note, having a security feature according to any of items 11 to 20.
22. (Preferred) The value document according to item 21, wherein the value document has a substrate made of paper and/or plastic.

The substrate can be e.g. a paper substrate, a plastic substrate or a paper/plastic multilayer substrate, such as a plastic/paper/plastic substrate or a paper/plastic/paper substrate. A plastic/paper/plastic substrate is understood to be a substrate having a middle paper ply which is furnished on both sides with a plastic ply or foil (see WO 2004/028825 A2). A paper/plastic/paper substrate is known from WO 2006/066431 A1.

23. (Preferred) The value document according to item 21 or 22, wherein the security feature is incorporated into the volume of the value document and/or applied to the value document.
24. (Fourth aspect) A method for checking the origin of the value document according to any of items 21 to 23, comprising the step of detecting the marker by means of a spatially resolving analytical method which is adapted to resolve down to the single-particle level.
25. (Preferred) The method according to item 24, wherein the spatially resolving analytical method is confocal laser microscopy or multiphoton microscopy.
26. (Preferred) The method according to item 24, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.

DETAILED DESCRIPTION OF THE INVENTION

Value documents within the context of this invention are objects such as bank notes, checks, shares, value stamps, identity cards, passports, credit cards, deeds and other documents, labels, seals, and objects to be safeguarded such as for example CDs, packages and the like. The preferred area of application is bank notes which are in particular based on a paper substrate.

The feature substance to be marked, present in particular in pulverized form, and suitable for the authentication of value documents, can be e.g. a luminescent feature substance, an IR absorber, an electrically conductive feature substance, a feature substance with magnetic properties, a thermochromic feature substance or a feature substance absorbing and/or remitting in a special wavelength region.

Security features for value documents having a luminescent component on the basis of luminophores having specific properties in their emission and excitation are known, e.g. from WO 81/03507 A1, EP 0 966 504 B1, WO 2011/084663 A2, DE 198 04 021 A1 and DE 101 11 116 A1. Such a security feature can be added in the form of a powder to the paper pulp during the manufacture of the paper-based value-document substrate. Furthermore, the security feature can be added in the form of a powder to a printing ink, with the printing ink being applied to the value-document substrate in a subsequent step. It is also possible to apply the printing ink to a foil element applied to the value-document substrate. The foil element may be e.g. a strip-shaped or a patch-shaped foil element.

Instead of the term "feature substance", the term "feature" will simply only be chosen at some places in the description. The "luminescent feature substance" will also be designated as "luminescent component" or "luminescent feature" in the description.

The luminescent feature substance to be marked can be based in particular on a matrix-forming inorganic solid which is doped with one or more rare earth metals or transition metals.

Suitable inorganic solids that are suitable for forming a matrix are for example:

oxides, in particular tri- and tetravalent oxides such as e.g. titanium oxide, aluminum oxide, iron oxide, boron oxide, yttrium oxide, cerium oxide, zirconium oxide, bismuth oxide, as well as more complex oxides such as e.g. garnets, including e.g. yttrium iron garnets, yttrium aluminum garnets, gadolinium gallium garnets;

perovskites, including yttrium aluminum perovskite, lanthanum gallium perovskite; spinels, including zinc aluminum spinels, magnesium aluminum spinels, manganese iron spinels; or mixed oxides such as e.g. ITO (indium tin oxide);

oxyhalides and oxychalcogenides, in particular oxychlorides such as e.g. yttrium oxychloride, lanthanum oxychloride; as well as oxysulfides, such as e.g. yttrium oxysulfide, gadolinium oxysulfide;

sulfides and other chalcogenides, e.g. zinc sulfide, cadmium sulfide, zinc selenide, cadmium selenide;

sulfates, in particular barium sulfate and strontium sulfate;

phosphates, in particular barium phosphate, strontium phosphate, calcium phosphate, yttrium phosphate, lanthanum phosphate, as well as more complex phosphate-based compounds such as e.g. apatites, including calcium hydroxyl apatites, calcium fluorapatites, calcium chlorapatites; or spodiosites, including e.g. calcium fluorospodiosites, calcium chlorospodiosites;

silicates and aluminosilicates, in particular zeolites such as e.g. zeolite A, zeolite Y; zeolite-related compounds such as e.g. sodalites; feldspars such as e.g. alkali feldspars, plagioclases;

further inorganic compound classes such as e.g. vanadates, germanates, arsenates, niobates, tantalates.

It is preferred that the luminescent feature substance to be marked is present in the form of luminescent particles which emit in the non-visible spectrum, i.e. in the UV, NIR or IR region (the abbreviation "UV" designating the term "ultraviolet", the abbreviation "NIR" designating the term "near infrared", the abbreviation "IR" designating the term "infrared"). With regard to the incorporation of the luminescent particles into value documents, e.g. bank notes, it is preferred that the particles have a maximum grain size of 30 µm, particularly preferably a maximum grain size of 20 µm.

The present invention is based on the idea of safeguarding the in particular luminescent feature substance to be marked, by a special forensic marking through which e.g. different production batches, deliveries, manufacturers, or processors can be marked. The marking can be composed of one or more, in particular luminescent, markers or marker substances with a distinguishable spectral signature. The marker substances are added to the in particular luminescent feature substance to be marked in so small a quantity that their detection by conventional sensor means (in other words, their macroscopic detection, in particular their machine detection in bank-note processing) is not possible, and the properties of the in particular luminescent feature substance to be marked are not influenced in an application-relevant manner.

The content of the marker (i.e. of the marker particles) preferably lies in a range of 0.1 to 10 wt. %, particularly preferably in a range of 1 to 5 wt. %, based on the total weight of the marked feature substance.

It is preferred that the nominal area density (i.e. the number of the marker particles per unit area of the value document) of the marker particles whose size is ≥1 µm in the value document (e.g. a bank note) is in a range of 10 to $10^9$ particles per square centimeter, particularly preferably in a range of 100 to $10^5$ particles per square centimeter. Depending on the employed method and experimental setup, the number of marker particles that is actually detectable in the value document can then deviate downward from the nominally contained number slightly (e.g. by a factor of two) or also greatly (e.g. by a factor of 100).

The detection of the marker in the stage of employing the marked feature substance for safeguarding value documents is only possible by means of a spatially resolving analytical method that is adapted to resolve down to a single-particle basis. In this way one can guarantee distinguishability from other substances occurring in high number in the basic materials of value documents (e.g. brighteners, additives, fillers, substances from the sizing). On the other hand, the forensic marking can be distinguished in this way from impurities.

It is preferred to employ as a marker a luminescent marker substance, in particular a luminophore, so that the detection of the marker can be effected on the basis of luminescence. Analytical techniques allowing a spatially resolved single-particle examination would in this case be in particular confocal laser microscopy or multiphoton microscopy.

Furthermore, it is possible to employ as a marker a non-luminescent marker substance, e.g. a solid that can be identified on the basis of its crystalline phase or structure or its chemical composition. Analytical techniques allowing a spatially resolved single-particle examination would in this case be in particular spatially resolved X-ray diffraction (µXRD), spatially resolved Raman scattering (µRaman), energy-dispersive X-ray spectroscopy (EDX) or spatially resolved X-ray fluorescence analysis (µXRF).

Furthermore, a luminescent marker substance with a specific crystalline phase or structure or a specific chemical composition can also be used, so that an identification is possible both on the basis of the luminescence of the marker substance and on the basis of the structure and/or the chemical composition of the marker substance.

Hereinafter the case of marking a luminescent feature substance by means of a luminescent marker will be described somewhat more closely. The detection of the luminescent marker is preferably effected by means of confocal laser spectroscopy.

Since one typically assumes very low concentrations of the luminescent marker in a likewise (at least partly) luminescent value-document substrate, finding the marker particles and their unambiguous assignment are the core of the proof. The proof can be effected on the basis of the local occurrence (designated hereinafter as "localization") of the signal and/or on the basis of the utilization of one or more properties of the luminescent marker, namely, the emission bands, the excitation bands and the lifetime of luminescence:

Localization: Since the marker is present in the form of particles (with a preferred grain size (D99) in a range of 1 to 30 µm), the luminescence occurs in a locally concentrated manner. If one manages to resolve the particles by spatially resolved microscopic detection, one obtains a clear signal for identification. In application, e.g. a value document having a paper substrate in which the marked luminescent feature substance is contained, the marker particles are rare, i.e. well hidden, and do not influence the marked luminescent feature substance upon macroscopic detection based on luminescence measurement. In this connection, it is especially suitable to detect the marker by means of confocal laser microscopy or multiphoton microscopy, which both possess a very high spatial resolution while at the same time resolving spectrally.

Emission bands: The shape of the emission bands allows the recognition and identification of the marker. Preferably, said bands stand out relative to the background luminescence of the value-document substrate and of incorporated or applied brighteners. If the emission bands are narrow and distinctly structured compared to the other luminescences occurring in the value-document substrate, then recognition is distinctly facilitated. These properties can be utilized to guarantee an automated process for finding the particles on the basis of a spectral fingerprint. For example, in the case of confocal laser microscopy, the spectrum of each image point moved to can be compared to the stored spectrum of the marker. If the marker was skillfully selected, the method reliably yields the particle location and hides background and foreign luminescence.

Excitation bands: The excitation bands can also be present in structured form. It is of interest here to select the marker such that the excitation bands overlap as well as possible with at least one of the available exciting laser lines. If the marker has a plurality of excitation bands, one preferably chooses a band for excitation at which background and/or brightener in the value document is not, or only little, excited. This facilitates the finding of the marker particles in the case of a luminescent background.

Lifetime of luminescence: A further parameter that can be drawn on is the lifetime of luminescence. If one chooses e.g. phosphorescent markers (in particular with a lifetime >10 µs), the background can also be reduced by delaying the detection relative to the excitation.

It is preferred that the spectral properties (i.e. the emission bands and/or the excitation bands) of the luminescent marker and of the luminescent feature substance marked therewith do not mutually overlap, or overlap as little as possible. This can be obtained e.g. by the marker emitting in a spectral region in which the marked luminescent feature substance is invisible. If the excitation bands are also without utilizable overlap, marker and marked luminescent feature substance can be proven separately.

The invention will hereinafter be described on the basis of exemplary embodiments in connection with FIGS. 1 to 5.

EXEMPLARY EMBODIMENT 1

Detailed Description of Various Embodiments

A luminescent feature substance, based on rare earth-doped luminescent pigments, was compounded with a specific marker, so that the content of the marker amounted to less than 5 wt. % based on the total weight of the marked luminescent feature substance. The feature substance responsible for the proof of authenticity emits in the non-visible spectral region—distinctly separately from the marker. As a marker there was employed europium-doped luminescent pigments based on $Y_2O_2S$ (the composition $Y_2O_2S$:Eu being abbreviated hereinafter as "YSA"). Feature substance and marker have disjoint, i.e. non-overlapping, spectral properties. The grain size (D99) of the marker amounted to 20 μm. Starting out from a paper pulp in which the marked feature substance had been incorporated, a sheet of paper was manufactured in a sheet former. In an independent working step, the document was rated as authentic on the basis of the non-visible luminescence of the feature substance. A sample of the paper with a dimension of 3 cm×3 cm was subsequently examined in a certain region by means of confocal laser microscopy (Plan Apochromat 20×/0.8 M27; field of view 0.75 mm×0.75 mm; excitation wavelength: 458 nm; 17% maximum power).

Figure 1:
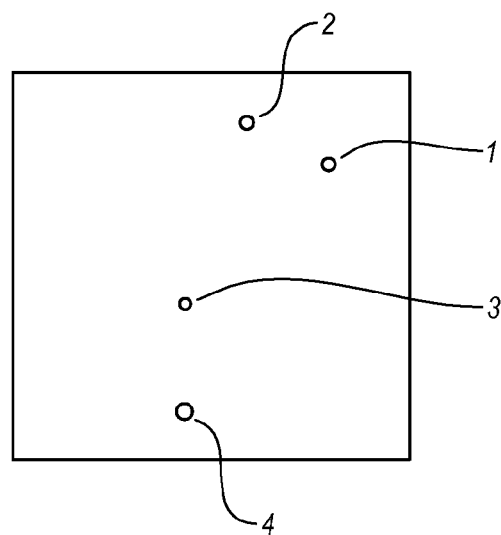
FIG. 1 the random distribution of three marker particles which all belong to a single type of marker within a section of a value-document substrate according to a first exemplary embodiment, FIG. 2 the emission spectra appurtenant to each of the three marker particles shown in FIG. 1 and measured by means of confocal laser microscopy, FIG. 3 the random distribution of three marker particles respectively belonging to another type of marker within a section of a value-document substrate according to a second exemplary embodiment, FIG. 4 the emission spectra appurtenant to each of the three marker particles shown in FIG. 3 and measured by means of confocal laser microscopy, FIG. 5 the XRD spectra of filler particles ($TiO_2$), feature particles ($ZrO_2$) and marker particles ($MoS_2$) that are measured on a value document according to a third exemplary embodiment by means of spatially resolved X-ray diffraction (μXRD).

FIG. 1 shows the spectroscopically examined paper region with a dimension of 0.75 mm×0.75 mm. The reference numbers 1, 2 and 3 designate three marker particles of the YSA marker. At the place with the reference number 4 the background luminescence was recorded.

Figure 2:
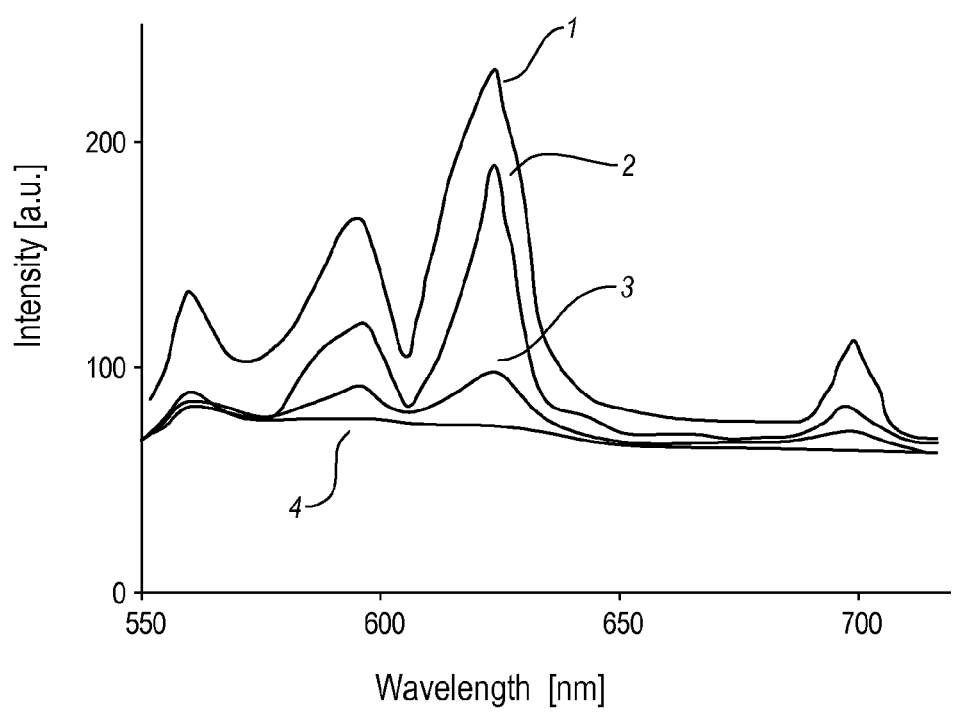

The emission spectra respectively appurtenant to the marker particles 1, 2 and 3 and the background 4 are shown in FIG. 2. The individual YSA marker particles can be unambiguously identified spectrally relative to the paper structure (i.e. the background 4). In addition, the intensity of the single particles is strong enough to resolve spectra.

EXEMPLARY EMBODIMENT 2

This exemplary embodiment illustrates the possibility of identifying a specific marker from a mixture of different markers. For this purpose, three different types of marker with a respective concentration of 0.25 wt. % and additionally a filler particle ($BaSO_4$) were incorporated in a paper. The examination conditions were identical with the conditions described hereinabove in the exemplary embodiment 1.

Figure 3:
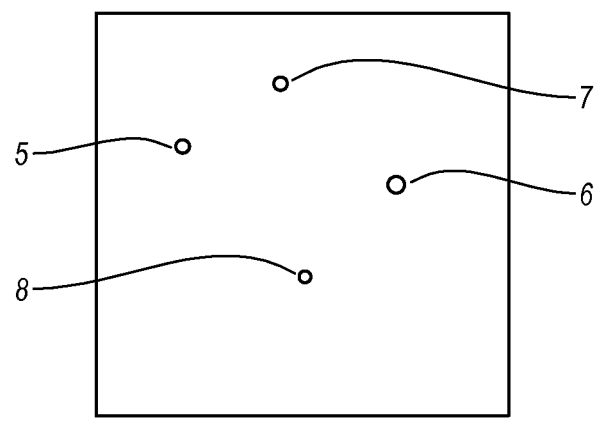

FIG. 3 shows the spectroscopically examined paper region with a dimension of 0.75 mm×0.75 mm. The reference numbers 5, 7 and 8 designate three marker particles respectively belonging to another type of marker. The reference number 6 designates a $BaSO_4$ filler particle of the paper.

Figure 4:
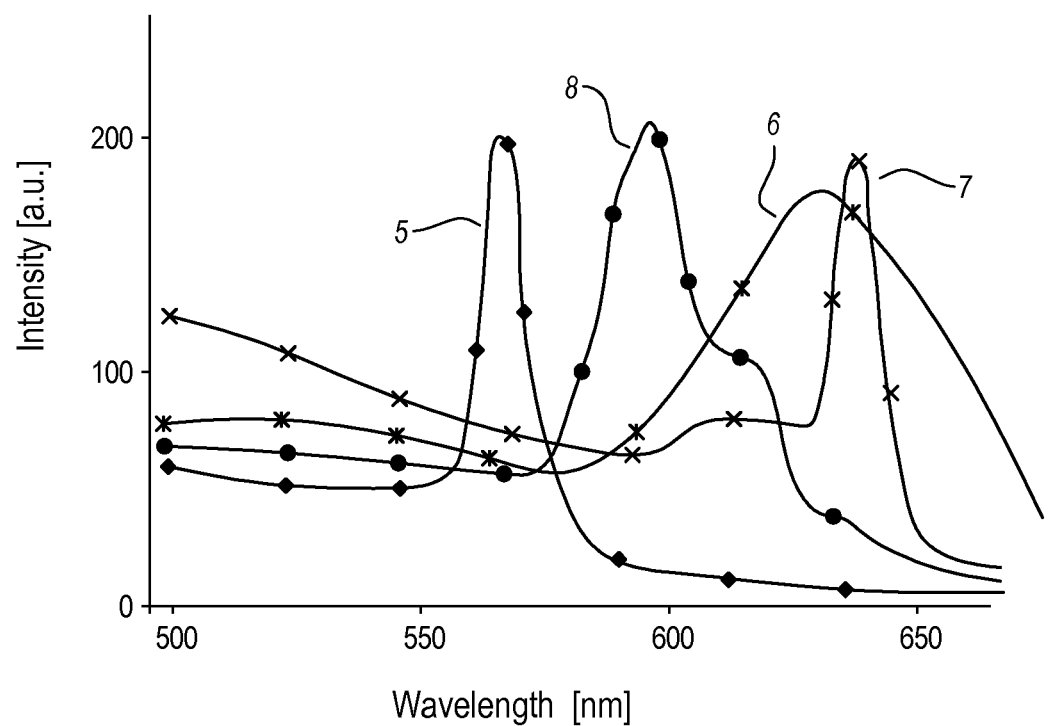

The emission spectra respectively appurtenant to the marker particles 5, 7 and 8 and the filler particle 6 are shown in FIG. 4. The figure indicates that the particles can be distinguished by means of confocal laser microscopy and unambiguously assigned on the basis of the shape of the spectra.

EXEMPLARY EMBODIMENT 3

This exemplary embodiment illustrates the realization of the invention using non-luminescent marker particles.

μXRD examination setups with a resolution in a range of several micrometers or several 100 nanometers, which is sufficient for a single-particle detection, are known in the prior art.

The characterization of a luminescent feature substance using the XRD pattern can be brought about by admixing a marker substance distinctly differing from the feature substance in the total XRD pattern, or also only in a prominent line. Since finely dispersed additives or fillers can be located within the value-document substrate, it is advantageous when the marker substance differs from the additives or fillers distinctly at least in a prominent line of the XRD pattern.

Figure 5:
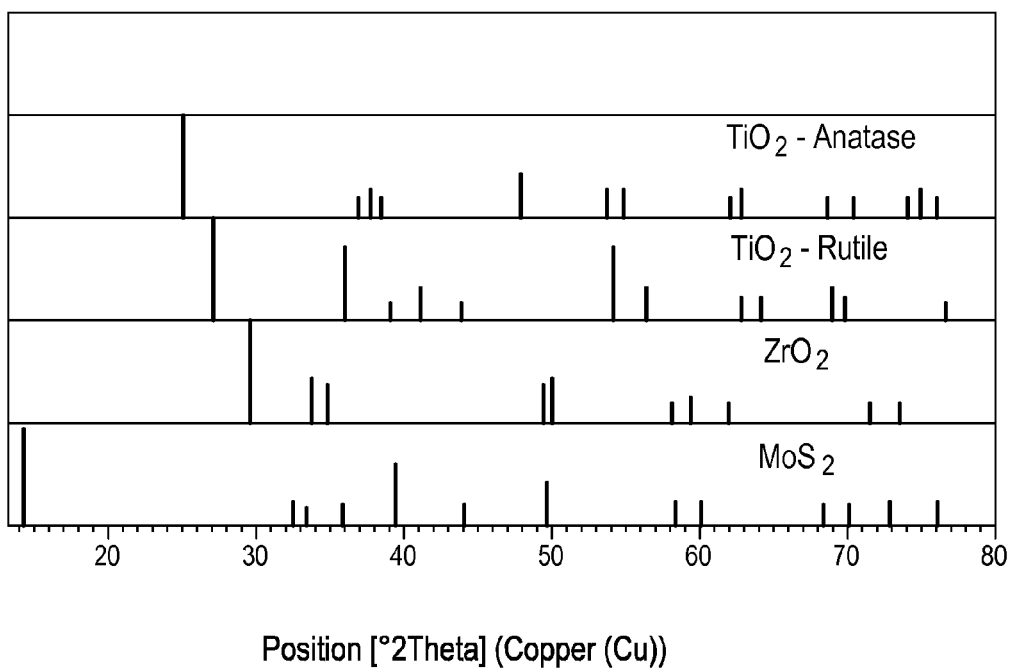

In this exemplary embodiment, a luminescent feature substance based on $ZrO_2$ was marked using $MoS_2$ particles as a marker substance and embedded into a paper. In the paper pulp there was finely dispersed $TiO_2$ in crystalline form (anatase or rutile form). In FIG. 5 are specified the XRD patterns of the different substances.

The two $TiO_2$ modifications present in the paper constitute a background which cannot be completely hidden even at high spatial resolution. Both the feature substance $ZrO_2$ and the marker substance $MoS_2$ possess an XRD signature distinctly distinguishable from the background.

By recording with high spatial resolution, the XRD signature of the marker substance can be recorded without disturbance through the feature substance $ZrO_2$, at most with a weak background through the $TiO_2$. In the present case, the proof of the marker and thus of the authenticity of the feature substance could also be furnished solely through the proof of the main line at approx. 14°.

EXEMPLARY EMBODIMENT 4

This exemplary embodiment illustrates a further realization of the invention using non-luminescent marker particles through employment of energy-dispersive X-ray spectroscopy (EDX) or spatially resolved X-ray fluorescence analysis (μXRF).

The marker selectively contains chemical elements that usually do not occur, and in particular not together, in the final application (i.e. in the value document). This marker substance is admixed to the luminescent feature substance. Via X-ray fluorescence there is determined the chemical composition on the single particle in the final application. A positive result is considered to be colocalization of the marker elements, i.e. finding the elements of the marker together at the same location.

In X-ray fluorescence, atoms are ionized by an exciting radiation (X-radiation or electron beams). The hole is filled by an electron stemming from a higher level. In this process there arises an X-radiation characteristic of the chemical element, which is detected in an energy-resolved manner.

As an element-specific analytical technique, X-ray fluorescence can be used down to a single-particle detection. Primarily two methods are realized technically. In the first method, X-ray fluorescence is triggered by X-ray irradiation (XRF, resolution in the μm region), in the second method by electron irradiation in the scanning electron microscope (EDX, resolution in the sub-μm region). In both techniques there is achieved a spatially resolved elemental analysis on the basis of the X-ray fluorescence spectrum of the elements in the measuring region. Hereinafter a marker application by means of spatially resolving XRF will be described by way of example:

The marker substance is a chemical compound (e.g. elemental oxides) of suitable elements, which compound can also be present in the form of a mixture of different stoichiometries. To achieve a marker function there are employed elemental combinations that occur at most in traces in the form of a chemical impurity, or not at all, both in the value document (in particular in the substrate) and in the feature substance. The elements typically occurring in a value document can be contained in the marker substance, but do not carry the information that is drawn on for rating the marker.

Typical elements occurring in a value document, from which a marker system must be delimited, are:

C, H, O (present in organic paper fibers), Ca (present in $CaCO_3$, white pigments), Ba, Ti, S (present in the fillers $TiO_2$ and $BaSO_4$), Al, Si (present in kaolins, fillers).

Suitable elements are chosen from the following group:

P, Cu, Mn, Fe, Zn, Ga, Ge, Br, Sr, Y, Zr, Nb, Mo, Ru, Rh, Pd, Ag, In, Sn, Ta, W, Au, Bi.

Particularly preferred are elements of the following group:

Mn, Fe, Cu, Zn, Ga, Ge, Br, Sr, Y, Zr, Nb, Mo, Ag, In, Sn.

To enable a reliable detection, at least two elements are preferably combined to a substance that can be incorporated in a stable manner and whose X-ray fluorescence bands lie distinctly separate and/or closely adjacent in the viewed spectral region. Overlapping bands are possible, but not preferred.

The following Table 1 summarizes the spectral position of the X-ray fluorescence bands Kα, Kβ, Lα, Lβ, Lγ (expressed in their characteristic energy in keV) of the stated elements. Especially suitable elements are highlighted by the sign "*" after the element symbol in column 2.

TABLE 1

| Atomic number | Symbol | Element | Kα (keV) | Kβ (keV) | Lα (keV) | Lβ (keV) | Lγ (keV) |
|---|---|---|---|---|---|---|---|
| 1 | H | Hydrogen | — | — | — | — | — |
| 6 | C | Carbon | 0.282 | — | — | — | — |
| 7 | N | Nitrogen | 0.392 | — | — | — | — |
| 8 | O | Oxygen | 0.526 | — | — | — | — |
| 13 | Al | Aluminum | 1.49 | 1.55 | — | — | — |
| 14 | Si | Silicon | 1.74 | 1.83 | — | — | — |
| 15 | P | Phosphorus | 2.02 | 2.14 | — | — | — |
| 16 | S | Sulfur | 2.31 | 2.46 | — | — | — |
| 20 | Ca | Calcium | 3.69 | 4.01 | 0.34 | — | — |
| 22 | Ti | Titanium | 4.51 | 4.93 | 0.45 | 0.46 | — |
| 25 | Mn * | Manganese | 5.90 | 6.49 | 0.64 | 0.65 | |
| 26 | Fe * | Iron | 6.40 | 7.06 | 0.70 | 0.72 | |
| 29 | Cu * | Copper | 8.04 | 8.90 | 0.93 | 0.95 | |
| 30 | Zn * | Zinc | 8.63 | 9.57 | 1.01 | 1.03 | |
| 31 | Ga * | Gallium | 9.24 | 10.26 | 1.10 | 1.12 | |
| 32 | Ge * | Germanium | 9.88 | 10.98 | 1.19 | 1.21 | |
| 35 | Br * | Bromine | 11.91 | 13.30 | 1.48 | 1.53 | |
| 38 | Sr * | Strontium | 14.15 | 15.85 | 1.81 | 1.87 | |
| 39 | Y * | Yttrium | 14.95 | 16.74 | 1.92 | 2.00 | |
| 40 | Zr * | Zirconium | 15.77 | 17.68 | 2.04 | 2.12 | 2.30 |
| 41 | Nb * | Niobium | 16.61 | 18.64 | 2.17 | 2.26 | 2.46 |
| 42 | Mo * | Molybdenum | 17.48 | 19.63 | 2.29 | 2.40 | 2.62 |
| 47 | Ag * | Silver | 22.16 | 24.96 | 2.98 | 3.16 | 3.52 |
| 49 | In * | Indium | 24.21 | 27.30 | 3.29 | 3.49 | 3.92 |
| 50 | Sn * | Tin | 25.27 | 28.5 | 3.44 | 3.66 | 4.13 |
| 56 | Ba | Barium | 32.19 | 36.4 | 4.47 | 4.83 | 5.53 |
| 72 | Hf | Hafnium | 55.76 | 63.21 | 7.89 | 9.02 | 10.5 |
| 73 | Ta | Tantalum | 57.52 | 65.21 | 8.14 | 9.34 | 10.9 |
| 74 | W | Tungsten | 59.31 | 67.23 | 8.39 | 9.67 | 11.3 |
| 79 | Au | Gold | 68.79 | 77.97 | 9.70 | 11.44 | 13.4 |
| 83 | Bi | Bismuth | 77.10 | 87.34 | 10.84 | 13 | |

Example 1: $TiO_2$-Loaded Paper, $SrSnO_3$ as Marker, Measurement by XRF

Upon the paper manufacture the feature substance containing 2 wt. % of marker substance is incorporated. The nominal concentration of the feature substance in the paper upon the manufacture of the paper amounts to 0.5 wt. %.

The marker substance chosen was $SrSnO_3$, the filler is $TiO_2$. The analytical technique XRF yields the signals of the elements Sr and Sn distinctly at 45 keV excitation energy in the emission energy range of 10 keV to 40 keV (see Table 2).

TABLE 2

| Element | Line | Energy (keV) | Signal (counts) | Remarks |
|---|---|---|---|---|
| Strontium (Sr) | Kα | 14.15 | 3518 | |
| | Kβ | 15.85 | 530 | |
| Tin (Sn) | Kα | 25.27 | 1320 | |
| | Kβ | 28.5 | 231 | |
| Titanium (Ti) | Kα | 4.51 | — | outside measuring region |
| | Kβ | 4.93 | — | |
| Background (for example paper fibers, unknown fillers) | | broad; maximum at 20.61 | 124 | maximum value of background |

In Example 1 the lines of the marker separate distinctly: while the element Sr emits primarily X-ray fluorescence between 14 and 16 keV, the element Sn shows its maximum emission in a distinctly higher energy range (25 to 29 keV).

Example 2

$BaSO_4$—$TiO_2$-loaded paper with printing, with the printing containing $CaCO_3$, a feature substance of unknown composition, and a marker; a second arbitrary feature substance is present in the paper substrate, with $CuGa_2O_4$ being employed as the marker of a first batch and $SrGa_2O_4$ as the marker of a second batch; the measurement was effected through employment of spatially resolved XRF.

Upon the paper manufacture the security feature is compounded from two batches, with 5 wt. % of marker substance $CuGa_2O_4$ and $SrGa_2O_4$ being contained, respectively. The nominal concentration of the compounded feature in the paper upon the manufacture of the paper amounts to 0.1 wt. %. Additionally it is known that a feature with marker was also incorporated in the printing ink. For the analysis the question arises of whether the compounded batch was already employed in the present test specimen.

The authenticity of the value document is proven unambiguously via the security elements. The properties of the printing can be ignored in this question. An unprinted region of the value document is examined for particles at ten places. Seven relevant particles are found and their elemental composition determined. Additionally, filler particles $BaSO_4$ and $TiO_2$ are found. In three particles the colocalization of Cu and Ga is proven, in three further ones the colocalization of Sr and Ga. A further particle contains Sr and Mo as elements.

From the result it can be concluded that a compounding of the known batches (marked with $SrGa_2O_4$ and $CuGa_2O_4$) was already used. Since the element Mo is not typical in a bank-note application, this element could be assigned to a further marker, for example $SrMoO_4$.

Lines of the stated elements that occur in the energy range between 4 keV and 20 keV are highlighted by the symbol "*" after the numerical value in the following Table 3.

TABLE 3

| Element | Kα [keV] | Kβ [keV] | Lα [keV] | Lβ [keV] | Lγ [keV] |
|---|---|---|---|---|---|
| Strontium Sr | 14.15* | 15.85* | 1.81 | 1.87 | |
| Copper Cu | 8.04* | 8.90* | 0.93 | 0.95 | |
| Gallium Ga | 9.24* | 10.26* | 1.10 | 1.12 | |
| Molybdenum Mo | 17.48* | 19.63* | 2.29 | 2.40 | 2.62 |
| Calcium Ca | 3.69* | 4.01* | 0.34 | — | — |
| Titanium Ti | 4.51* | 4.93* | 0.45 | 0.46 | |
| Barium Ba | 32.19 | 36.4 | 4.47* | 4.83* | 5.53* |

Example 3: $TiO_2$-Loaded Paper With a Mixture of $Bi_2W_2O_9$, $Bi_2W_3O_{12}$ and $BiW_2O_6$ as Marker; Measurement by XRF Upon the paper manufacture the security feature containing 2 wt. % of marker substance is incorporated. The nominal concentration of the feature in the paper upon the manufacture of the paper amounts to 1 wt. %.

The marker substance used is a mixture of $Bi_2W_2O_9$, $Bi_2W_3O_{12}$ and $BiW_2O_6$, the filler is $TiO_2$. The marker mixture contains particles with different quantity ratios of Bi/W. Such mixtures of different stoichiometries can arise for example also upon a poorly defined manufacture of the stated compounds. The analytical technique XRF yields sufficient information, at 45 keV excitation energy in the emission energy range up to 12 keV, to separate the fillers from the marker, although the X-ray fluorescence bands of the marker lie close together.

Lines of the stated elements that occur in the energy range between 6 keV and 20 keV are highlighted.

TABLE 4

| Element | Kα [keV] | Kβ [keV] | Lα [keV] | Lβ [keV] | Lγ [keV] |
|---|---|---|---|---|---|
| Tungsten W | 59.31 | 67.23 | 8.39* | 9.67* | 11.3* |
| Bismuth Bi | 77.10 | 87.34 | 10.8413* | 13.02* | 15.25* |
| Titanium Ti | 4.51 | 4.93 | 0.45 | 0.46 | |

The invention claimed is:

1. A method for marking a feature substance, present in pulverized form, with at least one marker, with the feature substance being suitable for authentication of value documents, comprising the step of mixing the feature substance with a small quantity of the marker present in form of particles, the small quantity of the marker lying in a range of 0.1 to 10 wt. % based on a total weight of the marked feature substance, so that macroscopic detectability and identifiability of the feature substance is not influenced by the marker and the marker is detectable in a value document having a security feature containing the marked feature substance by means of a spatially resolving analytical method which is adapted to resolve down to a single-particle level;
   wherein the feature substance is a luminescent feature substance and the marker is a luminescent marker;
   wherein an emission of the luminescent marker occurs in another spectral wavelength region compared to the emission of the marked luminescent feature substance, or
   wherein the luminescent marker is excitable in another spectral wavelength region than the marked luminescent feature substance.

2. The method according to claim 1, wherein the luminescent marker and the marked luminescent feature substance respectively have a different lifetime of luminescence.

3. The method according to claim 1, wherein a grain size (D99) of the marker lies in a range of 1 to 30 μm.

4. The method according to claim 1, wherein the spatially resolving analytical method is confocal laser microscopy or multiphoton microscopy.

5. The method according to claim 1, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.

6. The method according to claim 1, wherein the marker comprises a chemical compound including at least two elements selected from P, Cu, Mn, Fe, Zn, Ga, Ge, Br, Sr, Y, Zr, Nb, Mo, Ru, Rh, Pd, Ag, In, Sn, Ta, W, Au, and Bi.

7. A security feature for safeguarding of value documents, comprising a marked feature substance which is obtainable by mixing a feature substance present in pulverized form, and suitable for authentication of value documents, with a small quantity of a marker present in form of particles, the small quantity of the marker lying in a range of 0.1 to 10 wt. % based on a total weight of the marked feature substance, so that macroscopic detectability and identifiability of the feature substance is not influenced by the marker and the marker is detectable in a value document having the security feature by means of a spatially resolving analytical method which is adapted to resolve down to a single-particle level;
   wherein the feature substance is a luminescent feature substance and the marker is a luminescent marker;

wherein an emission of the luminescent marker occurs in another spectral wavelength region compared to the emission of the marked luminescent feature substance, or wherein the luminescent marker is excitable in another spectral wavelength region than the marked luminescent feature substance.

8. The security feature according to claim 7, wherein the luminescent marker and the marked luminescent feature substance respectively have a different lifetime of luminescence.

9. The security feature according to claim 7, wherein a grain size (D99) of the marker lies in a range of 1 to 30 μm.

10. The security feature according to claim 7, wherein the spatially resolving analytical method is confocal laser microscopy or multiphoton microscopy.

11. The security feature according to claim 7, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.

12. A value document having a security feature according to claim 7.

13. The value document according to claim 12, wherein the value document has a substrate made of paper and/or plastic.

14. The value document according to claim 12, wherein the security feature is incorporated into the volume of the value document and/or applied to the value document.

15. A method for checking the origin of the value document according to claim 12, comprising the step of detecting the marker by means of a spatially resolving analytical method which is adapted to resolve down to the single-particle level.

16. The method according to claim 15, wherein the spatially resolving analytical method is confocal laser microscopy or multiphoton microscopy.

17. The method according to claim 15, wherein the spatially resolving analytical method is chosen from the group consisting of spatially resolved X-ray diffraction, spatially resolved Raman scattering, energy-dispersive X-ray spectroscopy and spatially resolved X-ray fluorescence analysis.

18. The value document according to claim 7, wherein the marker comprises a chemical compound including at least two elements selected from P, Cu, Mn, Fe, Zn, Ga, Ge, Br, Sr, Y, Zr, Nb, Mo, Ru, Rh, Pd, Ag, In, Sn, Ta, W, Au, and Bi.

* * * * *